US00PP29529P2

(12) United States Plant Patent
Stemkens

(10) Patent No.: US PP29,529 P2
(45) Date of Patent: Jul. 17, 2018

(54) ***GAILLARDIA* PLANT NAMED 'GAIZ0007'**

(50) Latin Name: *Gaillardia aristata*
Varietal Denomination: GAIZ0007

(71) Applicant: SYNGENTA PARTICIPATIONS AG, Basel (CH)

(72) Inventor: Henricus Godefridus Wilhelmus Stemkens, Enkhuizen (NL)

(73) Assignee: Syngenta Participations AG, Basel (CH)

( * ) Notice: Subject to any disclaimer, the term of this patent is extended or adjusted under 35 U.S.C. 154(b) by 42 days.

(21) Appl. No.: 15/330,269

(22) Filed: Sep. 1, 2016

(51) Int. Cl.
*A01H 5/02* (2018.01)

(52) U.S. Cl.
USPC ..... Plt./431

(58) Field of Classification Search
USPC ..... Plt./431
See application file for complete search history.

*Primary Examiner* — Keith O Robinson
(74) *Attorney, Agent, or Firm* — Dale Skalla

(57) ABSTRACT

A new *Gaillardia* plant named 'GAIZ0007' particularly distinguished by the compact, mounding plant habit and the small inflorescences of a yellow-orange and yellow color and mostly the indeterminate flowering.

1 Drawing Sheet

Latin name of the genus and species of the plant claimed: *Gaillardia aristata.*

Varietal denomination: 'GAIZ0007'.

BACKGROUND OF THE NEW PLANT

The present invention comprises a *Gaillardia* plant, botanically known as *Gaillardia aristata*, and hereinafter referred to by the variety name 'GAIZ0007'.

'GAIZ0007' is a product of a planned breeding program. The new cultivar has small sized, orange-eyed, two-toned, yellow-orange and yellow inflorescences held just above the foliage, medium to deep green small foliage, medium sized and mounding plant habit with very good branching. The flowering habit of the new plant is indeterminate whereas most *Gaillardia* are terminate flowering.

'GAIZ0007' originated from an open pollination occurring in the summer of 2011 in a controlled environment in Enkhuizen, The Netherlands. The female parent was an unpatented plant, identified as 'N6038-1', having yellow and red inflorescences and a more vigorous and more upright plant habit than 'GAIZ0007'.

The male parent was an unpatented plant, identified as 'N6039-1', having peach-colored inflorescences and a more vigorous and more semi-upright plant habit than 'GAIZ0007'.

The resulting seeds were sown in Enkhuizen, The Netherlands in March 2012. 'GAIZ0007' was selected as one flowering plant (designated 'P4909-2') within the progeny of the stated cross in July 2012.

The first act of asexual reproduction of 'GAIZ0007' was accomplished when vegetative stem tip cuttings were propagated from the initial selection in October 2012 in a controlled environment in Enkhuizen, The Netherlands.

BRIEF DESCRIPTION OF THE PHOTOGRAPHS

The accompanying photographic drawings show typical flower and foliage characteristics of 'GAIZ0007' with colors being as true as possible with an illustration of this type.

Figure 1:
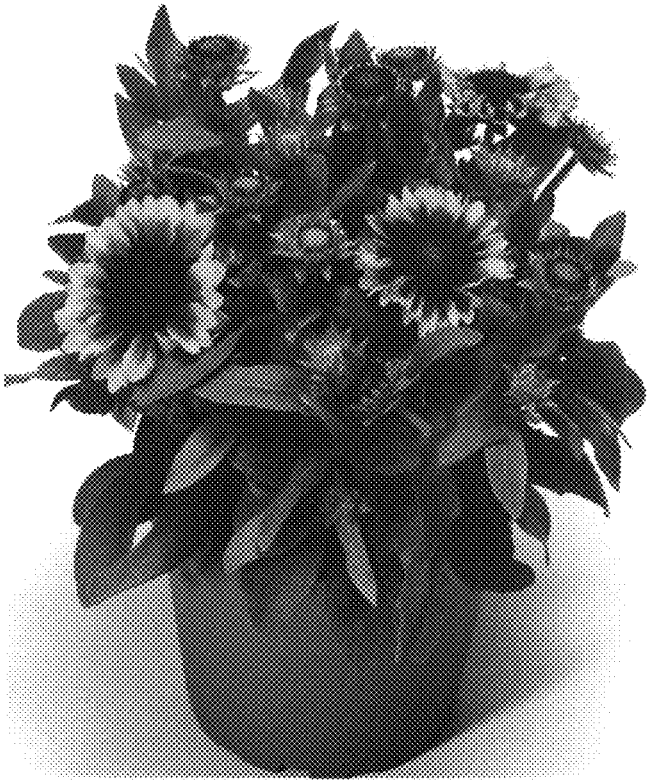
Figure 2:
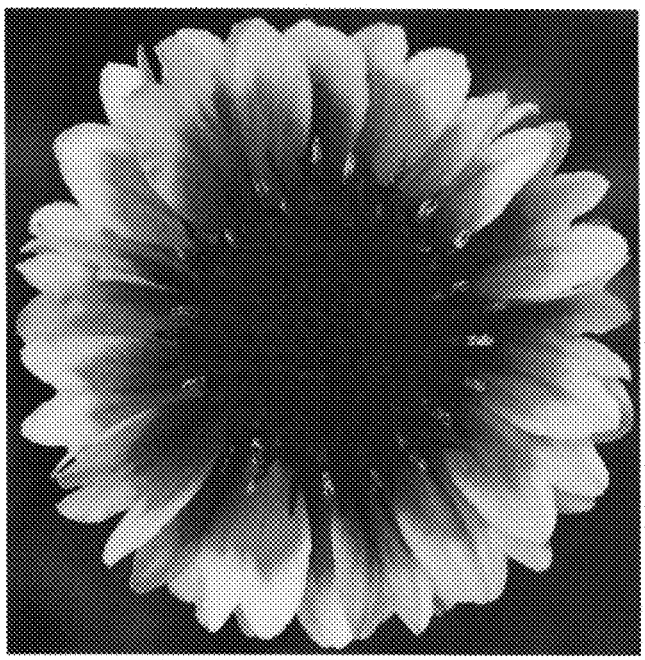

The photographic drawings show in FIG. 1 a whole flowering plant of the new variety and in FIG. 2 a close-up of the inflorescence.

DETAILED BOTANICAL DESCRIPTION

The aforementioned photographs were taken in July 2015 from plants grown in outdoor trial in Enkhuizen, The Netherlands. These plants were grown in 13 cm pots and were approximately 3 months old.

'GAIZ0007' has not been made publicly available prior to the effective filing date of this application, notwithstanding any disclosure that may have been made less than one year prior to the effective filing date of this application by the inventor or another who obtained 'GAIZ0007' directly from the inventor.

The plant descriptions and measurements were taken in Enkhuizen, The Netherlands on Jul. 15, 2016 using 12-13 week old plants from an outdoor trial field. Cultivation of these plants had started in early June 2016 with planting rooted cuttings into 13 cm pots and growing them on the ground under natural outdoor conditions through the summer months.

Color references are made to The Royal Horticultural Society Colour Chart (R.H.S.) 2001

TABLE 1

DIFFERENCES BETWEEN THE NEW VARIETY 'GAIZ0007' AND A SIMILAR VARIETY

| | 'GAIZ0007' | 'Gallo Dark Bicolor' ('KIEGALDAB' U.S. Plant Pat. No. 20,718) |
|---|---|---|
| Flower diameter: | 6 cm | 10 cm |
| Flowering: | Indeterminate | Determinate |
| Leaf size: | Small | Large |

Plant:

*Type*.—Perennial, herbaceous, continuously flowering through the summer months, vernalization not essential for initiating of flowering, hardiness tolerates temperature above minus 10° centrigrades temperature (frost).

*Form, growth and habit*.—Upright, tight and well-branched habit, relatively compact and small in size with the flower heads just above the foliage canopy.

*Plant height* (*without inflorescences*).—12-14 cm.

*Plant height* (*inflorescence included*).—18.5 cm.

*Plant width*.—22.0 cm.

Roots:

*Number of days to initiate and develop roots*.—16-18 days at about 22 degrees C.

*Type*.—Fine, fibrous, free branching.

*Color*.—RHS N155C.

Foliage:

*Arrangement*.—Alternate, simple leaves.

*Immature, leaf color, upper surface*.—RHS 137B.

*Lower surface*.—RHS 138B.

*Mature, leaf color, upper surface*.—RHS 147B.

*Lower surface*.—RHS 147B.

*Length*.—4-5 cm.

*Width*.—1.0-1.2 cm.

*Shape*.—Lanceolate to linear.

*Base shape*.—Attenuate.

*Apex shape*.—Acute.

*Margin*.—Entire.

*Texture, both surfaces*.—Smooth.

*Color of veins, upper surface*.—RHS 144B near base to RHS 145B.

*Color of veins, lower surface*.—RHS 144A.

*Petiole color*.—Sessile, no petiole.

Stem:

*Quantity of main branches per plant*.—18, each with 2 to 4 secondary branches.

*Color of stem*.—RHS 144A.

*Stem length*.—About 11.0 cm.

*Stem diameter*.—0.4 cm.

*Length of internodes*.—1.5-2.5 cm.

*Texture*.—Hairy, pilose.

Peduncle:

*Color of peduncle*.—RHS 144B.

*Length of peduncle*.—About 5.0-6.0 cm.

*Peduncle diameter*.—0.25-0.3 cm.

*Texture*.—Very fine pubescent.

Inflorescence:

*Type*.—Capitulum, single inflorescences, borne terminally on short peduncles above the foliage.

*Quantity of inflorescences per plant*.—About 70 inflorescences.

*Lastingness of individual blooms on the plant*.—About two weeks depending on temperature.

*Fragrance*.—None.

Bud (just when opening/showing color):

*Color*.—RHS 7B and RHS 143C.

*Length*.—1-1.1 cm.

*Width*.—1.1-1.3 cm.

*Shape*.—Cup-shaped.

*Texture*.—Covered with fine pubescence and with long hair on phyllaries.

Young inflorescence:

*Diameter*.—About 3.2-3.5 cm.

*Color of rays*.—Approximately RHS 46B with yellow ring RHS 14B.

*Color of rays, lower side*.—From RHS 13B and RHS 46B.

*Color of 'disc' with the disc florets still closed*.—RHS 187C and RHS N144A.

Mature inflorescence:

*Shape*.—Medium sized, daisy-type inflorescences with two whorls of ray florets surrounding the disc, and more or less horizontally directed.

*Diameter of whole inflorescence*.—6 cm.

*Diameter of 'disc'*.—2.3-2.5 cm.

*Diameter of receptacle*.—3.5 cm.

Ray florets:

*Average quantity of ray florets*.—20-24, in two whorls.

*Color of floret, upper surface*.—RHS 46B with yellow ring, RHS 14A.

*Color of lower surface*.—RHS 13B and RHS 46B.

*Length*.—2 cm.

*Width*.—1 cm.

*Shape*.—Ligulate to weakly oblanceolate.

*Apex shape*.—Obtuse.

*Margin*.—Entire.

*Texture, upper surface*.—Glabrous.

*Texture, lower surface*.—Fine pubescent.

Disc florets:

*Average quantity of disc florets*.—100.

*Shape*.—Tube-shaped.

*Apex shape*.—5-pointed with acute tips.

*Color of young disc florets, at apex*.—RHS 187A.

*Color of open floret*.—RHS 185A, corolla of RHS 187D.

*Length of floret*.—1 cm.

*Width at apex*.—0.4 cm.

Involucre/receptacle:

*Shape*.—Flattened semi-sphere, formed by the phyllaries in an overlapping arrangement.

*Diameter* (*width*).—3.4 cm.

*Diameter* (*depth*).—1.2 cm.

Phyllaries:

*Quantity of phyllaries*.—45.

*Shape*.—Lanceolate.

*Apex shape*.—Acuminate.

*Base*.—Sessile, fused with receptacle.

*Margins*.—Entire.

*Color, outer surface*.—RHS 147B.

*Color, inner side*.—RHS 147B.

*Length*.—1.4 cm.

*Width*.—0.4 cm.

*Texture outer surface*.—Densely pubescent.

*Texture inner surface*.—Densely pubescent.

Reproductive organs:

*Gynoecium*.—Developed in disc florets.

*Pistil, number per floret*.—One.

*Pistil, length*.—1.2 cm.

*Style color*.—RHS 12A.

*Style length*.—0.5 cm.

*Stigma color*.—RHS 187A.

*Stigma shape*.—Bi-lobed.

*Stigma, length*.—0.6 cm.

*Ovary, length*.—0.1 cm.

*Androecium*.—Present in disk florets only.

*Number of stamen*.—4 per floret, tube.

*Filaments*.—Free filaments, united anthers.

*Anther, shape*.—Linear, 4 mm in length.

*Anther color*.—RHS 157D at base, rest is RHS 17C.

*Pollen amount*.—Moderate.

*Color of pollen*.—RHS 17B.

*Fertility/seed set*.—Has not been observed on this hybrid.

*Disease/pest resistance*.—Has not been observed on this hybrid.

What is claimed is:

1. A new and distinct variety of *Gaillardia* plant named 'GAIZ0007' substantially as illustrated and described herein.

* * * * *